(12) United States Patent
Wei et al.

(10) Patent No.: US 9,132,240 B2
(45) Date of Patent: Sep. 15, 2015

(54) INJECTION PEN FOR INTRADERMAL MEDICATION INJECTION

(75) Inventors: Min Wei, Morris Plains, NJ (US); Ying Xu, Hackensack, NJ (US); James Bates, Sparta, NJ (US); Kenneth G Powell, Raleigh, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 573 days.

(21) Appl. No.: 13/127,451

(22) PCT Filed: Nov. 6, 2009

(86) PCT No.: PCT/US2009/006012
§ 371 (c)(1),
(2), (4) Date: Jul. 14, 2011

(87) PCT Pub. No.: WO2010/053569
PCT Pub. Date: May 14, 2010

(65) Prior Publication Data
US 2011/0270222 A1  Nov. 3, 2011

Related U.S. Application Data

(60) Provisional application No. 61/193,233, filed on Nov. 7, 2008.

(51) Int. Cl.
*A61M 5/00* (2006.01)
*A61M 5/315* (2006.01)
*A61M 5/24* (2006.01)

(52) U.S. Cl.
CPC ....... *A61M 5/31585* (2013.01); *A61M 5/31551* (2013.01); *A61M 5/24* (2013.01);

(Continued)

(58) Field of Classification Search
CPC ................. A61M 5/31551; A61M 2005/2407; A61M 5/3156; A61M 5/315; A61M 5/31593; A61M 5/31541; A61M 5/3155; A61M 5/31558
USPC ......... 604/211, 207–210, 181, 187, 232–234, 604/61–64
See application file for complete search history.

(56) References Cited

U.S. PATENT DOCUMENTS

| | | | | |
|---|---|---|---|---|
| 5,582,598 A | * | 12/1996 | Chanoch | 604/208 |
| 5,728,074 A | | 3/1998 | Castellano | |
| 6,001,089 A | * | 12/1999 | Burroughs et al. | 604/506 |
| 6,095,572 A | * | 8/2000 | Ford et al. | 285/361 |
| 7,290,573 B2 | * | 11/2007 | Py et al. | 141/329 |

FOREIGN PATENT DOCUMENTS

| | | |
|---|---|---|
| JP | 56-20465 | 2/1981 |
| JP | 08-103495 | 4/1996 |

(Continued)

OTHER PUBLICATIONS

Official Notice of Rejection issued in JP Patent Application No. 2011-535560 dated Sep. 10, 2013.

*Primary Examiner* — Phillip Gray
(74) *Attorney, Agent, or Firm* — Roylance, Abrams, Berdo & Goodman, L.L.P.

(57) ABSTRACT

A pen body assembly (100) for a drug delivery pen includes a pen body (101) and a dose setting body (111) movably connected to the pen body (101). A knob (109) is connected to the dose setting body (111) for moving the dose setting body (111) relative to the pen body (111). One of the pen body (101) and the dose setting body (111) has a thread groove (107) having a varied pitch disposed thereon and the other one has a protrusion (105) engaging the thread groove (107).

10 Claims, 12 Drawing Sheets

(52) U.S. Cl.

CPC ....... *A61M 5/31535* (2013.01); *A61M 5/31543* (2013.01); *A61M 5/31558* (2013.01); *A61M 5/31575* (2013.01); *A61M 2005/2407* (2013.01); *A61M 2005/2488* (2013.01); *A61M 2005/3152* (2013.01)

(56) References Cited

FOREIGN PATENT DOCUMENTS

| | | |
|---|---|---|
| JP | 2002541931 | 12/2002 |
| WO | 2010/053569 A1 | 5/2010 |

* cited by examiner

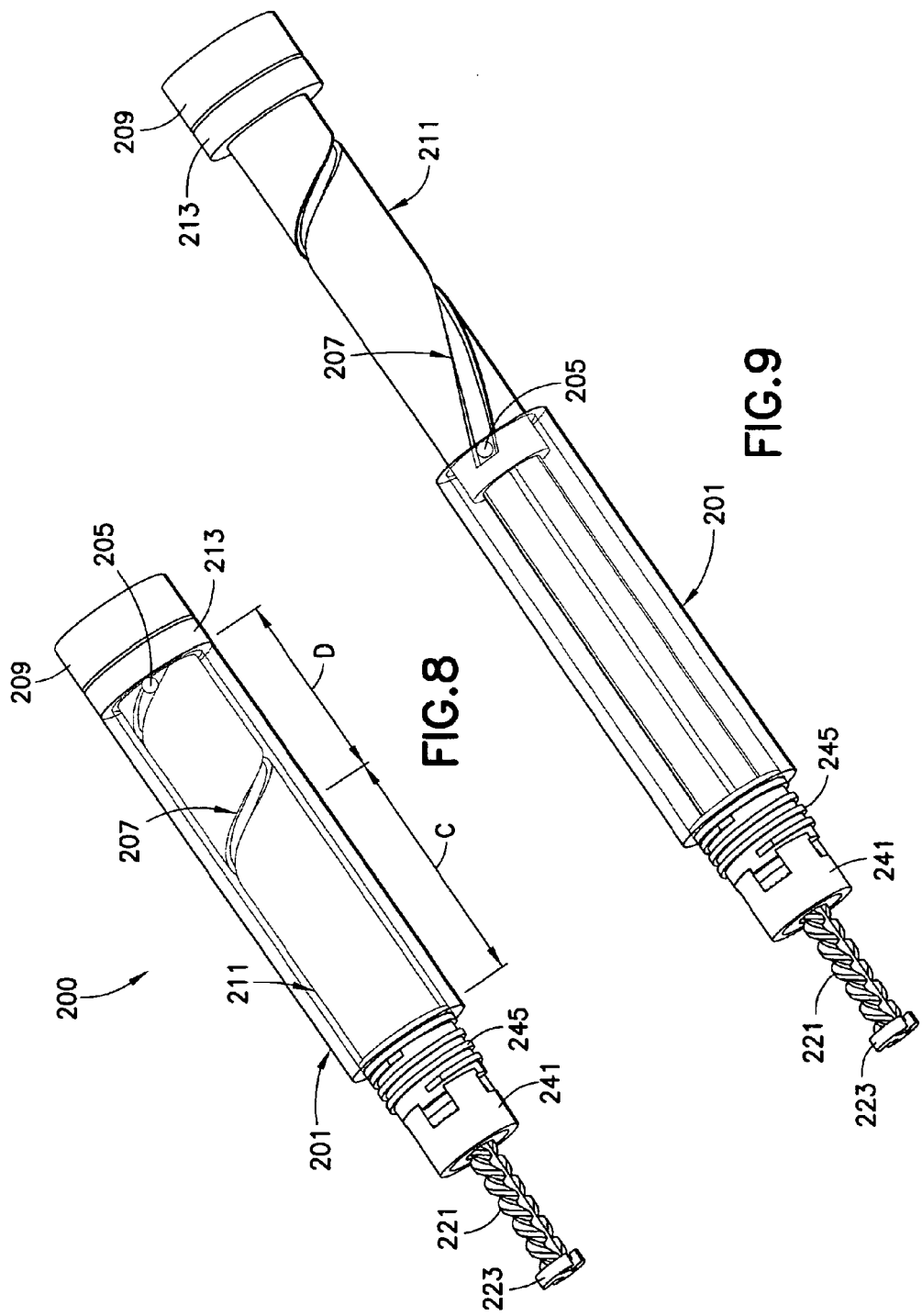

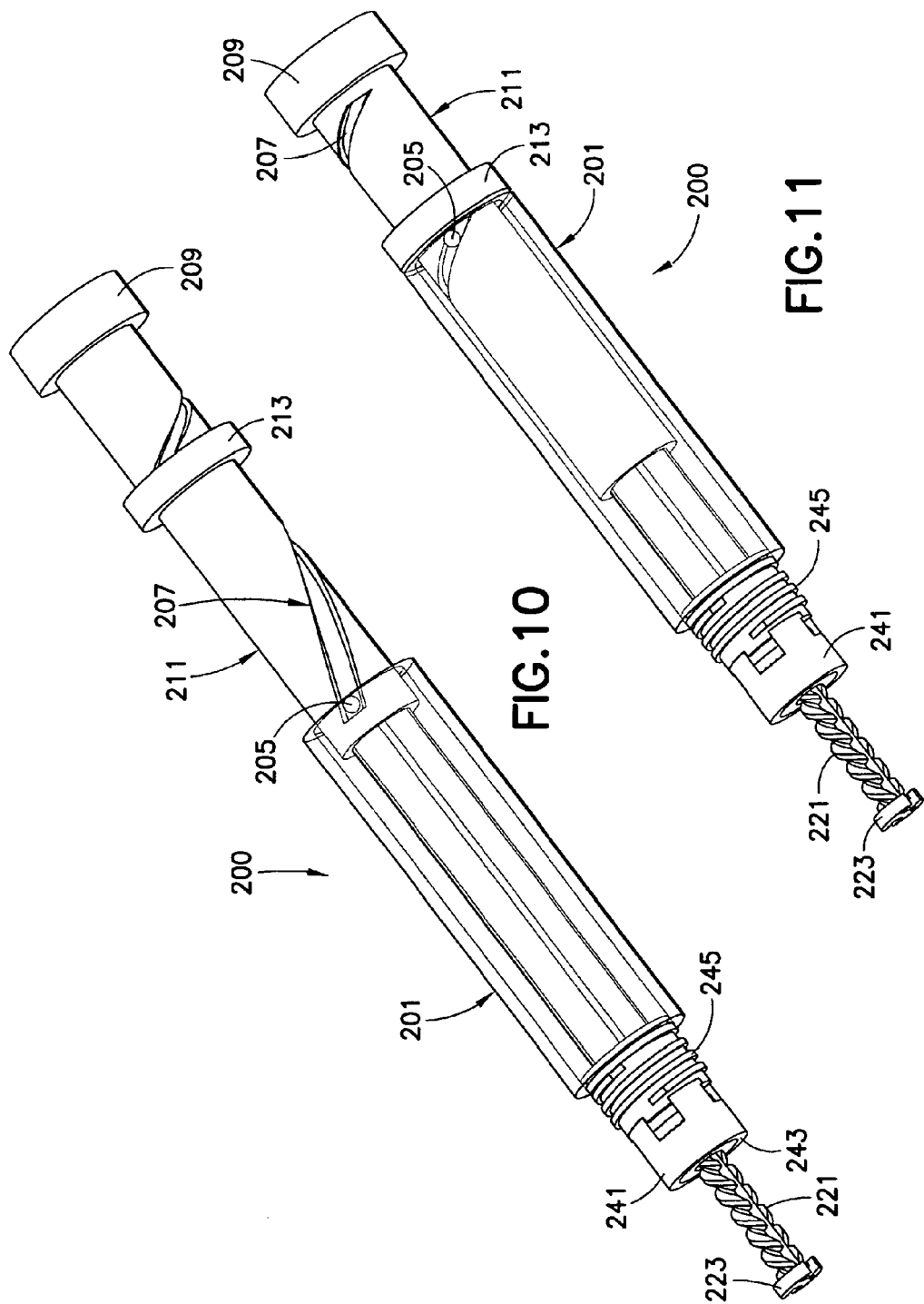

INJECTION PEN FOR INTRADERMAL MEDICATION INJECTION

CROSS REFERENCE TO RELATED APPLICATION

This application claims the benefit under 35 U.S.C. §119(e) of U.S. Provisional Application Ser. No. 61/193,233, filed Nov. 7, 2008, the entire disclosure of which is hereby incorporated by reference.

FIELD OF THE INVENTION

The present invention relates generally to a pen injector system in which dose setting threads have a variable pitch. More particularly, the present invention generally relates to a drug delivery pen having a pen injector system in which dose setting threads have a variable pitch to facilitate an intradermal medication injection. Still more particularly, the present invention provides a drug delivery pen in which variable pitch threads provide a mechanical advantage to reduce the required injection force for an intradermal medication injection.

BACKGROUND OF THE INVENTION

Insulin and other injectable medications are commonly given with drug delivery pens, whereby a disposable pen needle assembly is attached to facilitate drug container access and allow fluid egress from the container through the needle into the patient.

As technology and competition advance, driving the desire for shorter, thinner, less painful, and more efficacious injections, the design of the pen needle assembly and parts thereof becomes more and more important. Designs need to proactively address ergonomically improving injection technique, injection depth control and accuracy, the ability to be safely used and transported to disposal, and protection against misuse while maintaining the ability to be economically manufactured on a mass production scale.

The assembly and operation to a typical drug delivery pen, as shown in FIGS. 1 and 2, is described in U.S. Patent Application Publication No. 2006/0229562, published on Oct. 12, 2006 and in U.S. Pat. No. 6,24,095, issued on Jun. 19, 2001, both of which are hereby incorporated by reference in their entirety.

Drug delivery pens, such as the exemplary pen injector 100 shown in FIGS. 1 and 2, typically comprise a dose knob/button 24, an outer sleeve 13, and a cap 21. The dose knob/button 24 allows a user to set the dosage of medication to be injected. The outer sleeve 13 is gripped by the user when injecting medication. The cap 21 is used by the user to securely hold the pen injector device 100 in a shirt pocket, purse or other suitable location and provide cover/protection from accidental needle injury.

FIG. 2 is an exploded view of the drug delivery pen 100 of FIG. 1. The dose knob/button 24 has a dual purpose and is used both to set the dosage of the medication to be injected and to inject the dosed medicament via the leadscrew 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail here as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used, such as attaching to the cartridge. To protect a user, or anyone who handles the pen injection device 100, an outer cover 69, which attaches to the hub 20, covers the hub. An inner shield 59 covers the patient needle 11 within the outer cover 69. The inner shield 59 can be secured to the hub 20 to cover the patient needle by any suitable means, such as an interference fit or a snap fit. The outer cover 69 and the inner shield 59 are removed prior to use. The cap 21 fits snugly against outer sleeve 13 to allow a user to securely carry the drug delivery pen 100.

The medicament cartridge 12 is typically a glass tube sealed at one end with the septum 16 and sealed at the other end with the stopper 15. The septum 16 is pierceable by a septum penetrating cannula 18 in the hub 20, but does not move with respect to the medicament cartridge 12. The stopper 15 is axially displaceable within the medicament cartridge 12 while maintaining a fluid tight seal.

Intradermal drug delivery has provided many clinical advantages, from vaccine delivery to insulin delivery. An intradermal drug delivery is made by delivering the drug into the dermis layer of the skin. However, a higher injection pressure, up to 200 psi or higher, is occasionally needed to overcome back pressure from intradermal tissue, because it is not as soft as subcutaneous tissue, which is mainly fat tissues. To facilitate self-injection, a lower back pressure and smaller amount of force is preferred to make the injection. Thus, a need exists for a drug delivery pen that amplifies the input force to facilitate an intradermal medication injection.

The backpressure in subcutaneous injections is not very large, while the backpressure associated with intradermal injections may be many times greater than that of subcutaneous injections. For example, the backpressure often exceeds 200 psi for an intradermal injection, while the backpressure for a subcutaneous injection is generally in the range of 30-50 psi. Thus, a need exists for a drug delivery pen that has a high mechanical gain to reduce thumb forces required to overcome the initial high breakout force in the cartridge during an intradermal injection.

Existing drug delivery pens have limited mechanical advantage due to the requirements of subcutaneous delivery, which has a relatively low backpressure. However, as noted above, the backpressure associated with intradermal injections is substantially higher. Therefore, the drug delivery pen should have a much larger mechanical gain to allow a user to apply a comfortable thumb force, and to gain it up to a higher force on the cartridge stopper. However, the higher force is preferably needed during the first stage of the injection, i.e., the breakout force. After the initial breakout, the injection force is reduced to a significantly lower level and is substantially constant through the end of the injection.

Existing methods of performing high pressure injections use high pressure gas or strong springs to generate a high pressure to drive the plunger. However, such methods make it difficult to achieve a slow injection. Moreover, such methods have high manufacturing costs, which is not desirable for routine self-injections, such as insulin self-injections. Another method used is a triple start thread design to generate required constant force amplification. However, such generated force is not sufficient for an intradermal delivery force and also reduces the total dose range. Additionally, there are no existing devices that can be used with existing drug delivery pens to generate the required push force at the leadscrew with a reasonable thumb force being applied.

Accordingly, a need exists for a pen needle assembly for a drug delivery pen that facilitates intradermal medication injection.

SUMMARY OF THE INVENTION

In accordance with an aspect of the present invention, a drug delivery pen is provided including a pen injector system in which dose setting threads have a variable pitch to reduce the force required to intradermally inject medication.

An objective of the present invention is to reduce the thumb push force while maintaining the push force at an end of the leadscrew. This may be accomplished by increasing the pitch of the dose setting threads in the pen injector system. However, increasing the pitch may reduce the maximum dose deliverable by the drug delivery pen. By providing a variable pitch of the dose setting threads, a mechanical advantage is provided that reduces the required injection force. Therefore, an exemplary embodiment of the present invention varies the pitch of the dose setting threads of the pen injector system, thereby reducing the force required to perform an intradermal medication injection without compromising the maximum dose deliverable by the drug delivery pen. Additionally, a higher dose range is provided without increasing the length of the drug delivery pen.

A pen body assembly for a drug delivery pen according to an exemplary embodiment of the present invention includes a pen body and a dose setting body movably connected to the pen body. A knob is connected to the dose setting body for moving the dose setting body relative to the pen body. One of the pen body and the dose setting body has a thread groove having a variable pitch disposed thereon and the other one has a protrusion engaging the thread groove.

Objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will be more apparent from the following detailed description of exemplary embodiments of the present invention and from the accompanying figures, in which:

FIGS. 8-11 are perspective views of pen body assembly according to another exemplary embodiment of the present invention in which variable pitch threads are disposed on a pen body;

Throughout the drawings, like reference numbers will be understood to refer to like parts, components and structures.

DETAILED DESCRIPTION OF THE EXEMPLARY EMBODIMENTS

Figure 1:
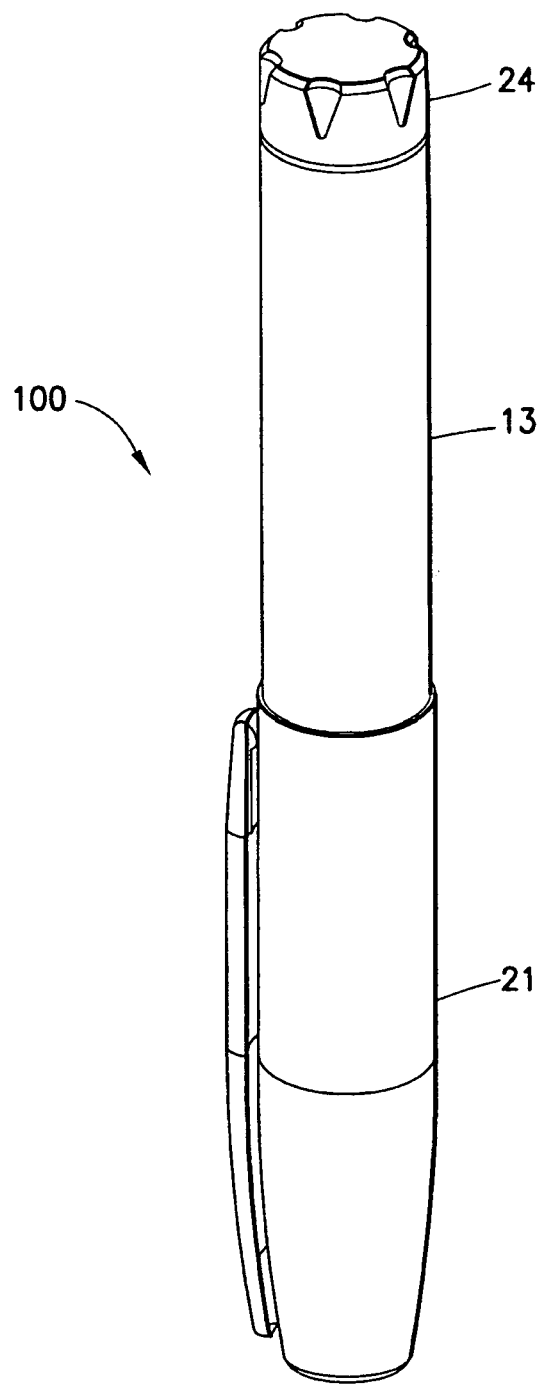
FIG. 1 is a perspective view of an assembled drug delivery pen.
Figure 2:
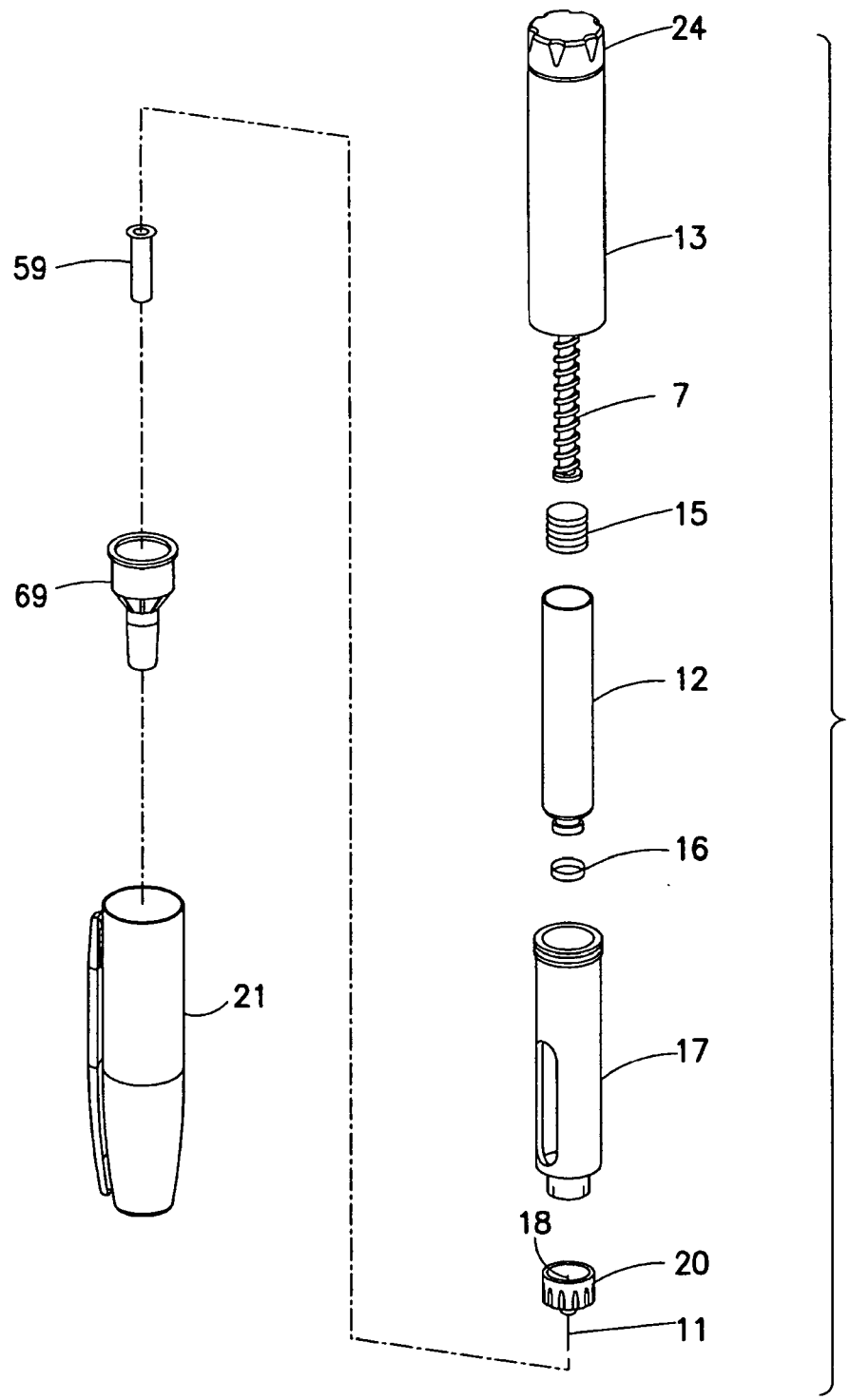
FIG. 2 is an exploded perspective view of the components of the drug delivery pen of FIG. 1.

The following description and details of exemplary embodiments of the present invention are generally disclosed with reference to a typical drug delivery pen 100, as shown in FIGS. 1 and 2. Another typical drug delivery pen is disclosed in U.S. Pat. No. 5,626,566, which issued May 6, 1997, and is hereby incorporated by reference in its entirety.

For intradermal drug delivery, an initial high injection force is often required to open the space in the dermis tissue layer to inject the medication. Thereafter the required injection force decreases. To accommodate this feature of intradermal medication injections, a variable pitch configuration may be used. As shown in FIGS. 4-7, the variable pitch threads may be disposed on the pen body 101. Alternatively, as shown in FIGS. 8-11, the variable pitch threads may be disposed on the dose setting knob body 111. By varying the pitch, the applied injection force is amplified while not reducing the maximum deliverable dose.

Figure 3:
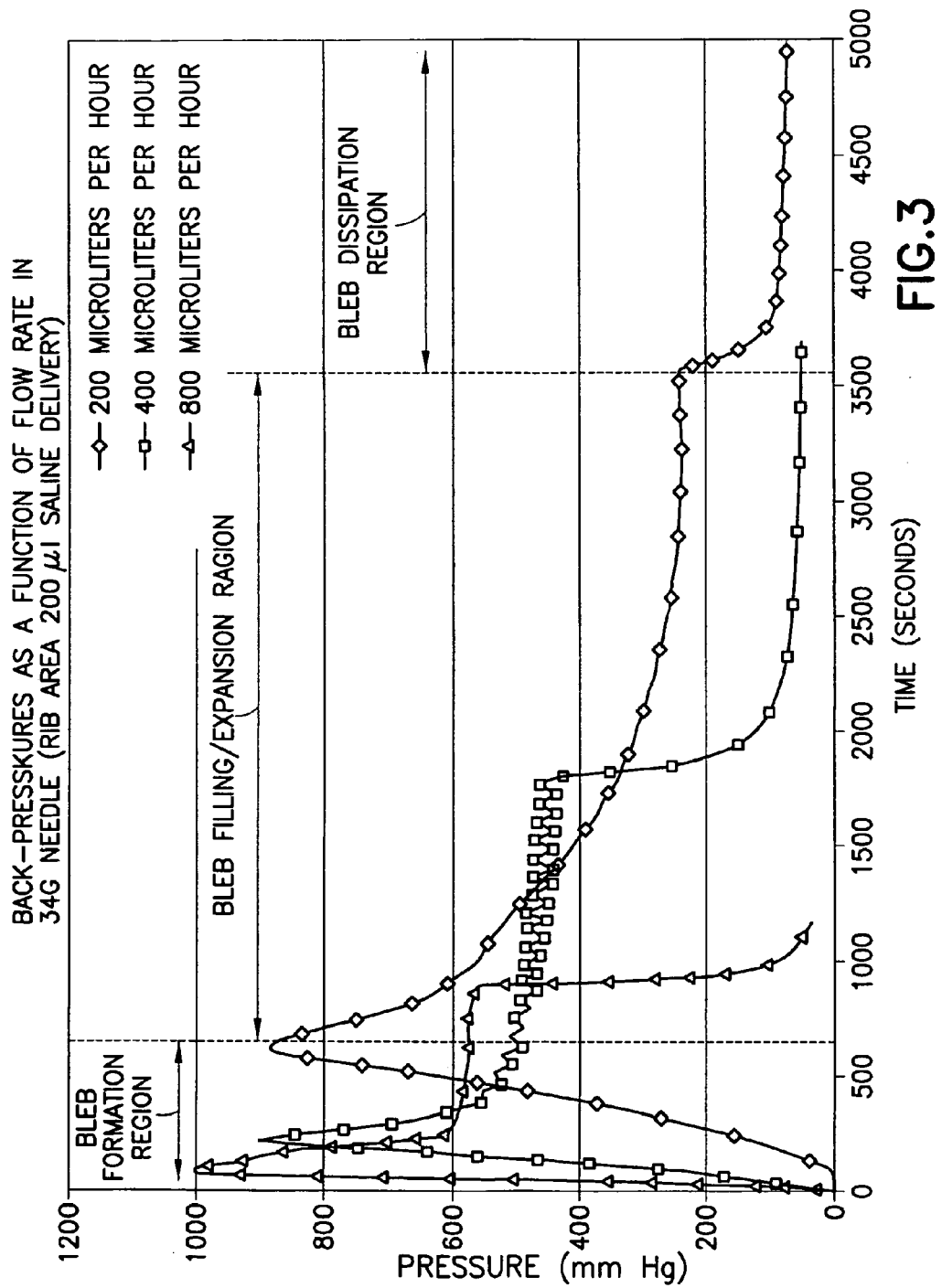
FIG. 3 is a graph of backpressures as a function of flow rate.

An exemplary embodiment of the present invention provides a drug delivery pen in which the pitch of the dose setting threads of the pen injector system is varied, thereby reducing the force required to perform an intradermal medication injection without compromising the maximum dose deliverable by the drug delivery pen. As shown in FIG. 3, the high back pressure peaks at the beginning of the injection and then levels off. The variable pitch design has a high pitch, i.e., more distance between threads, for the beginning portion of the injection (i.e., higher mechanical advantage and lower required pushing force), and then the pitch gradually changes to a smaller pitch, i.e., less distance between threads, in response to the lower required injection force, thereby substantially avoiding a reduction in the maximum dose deliverable by the drug delivery pen.

The variable pitch of the dose setting threads generates a high push force at an end 223 of the leadscrew 221 (FIG. 8), which is ideal for intradermal drug deliveries and other similar types of drug deliveries. Furthermore, this configuration maintains the maximum deliverable dose in the desired range to avoid having to perform multiple injections because of low dose capabilities.

Figure 4:
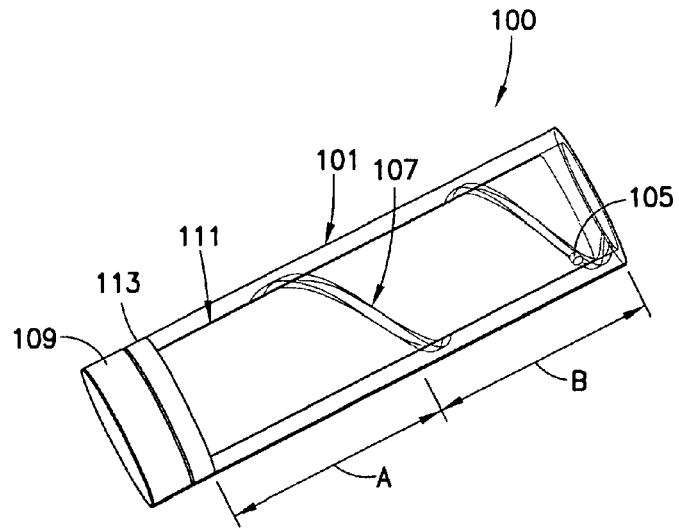
FIGS. 4-7 are perspective views of pen body assembly according to an exemplary embodiment of the present invention in which variable pitch threads are disposed on a pen body.
Figure 5:
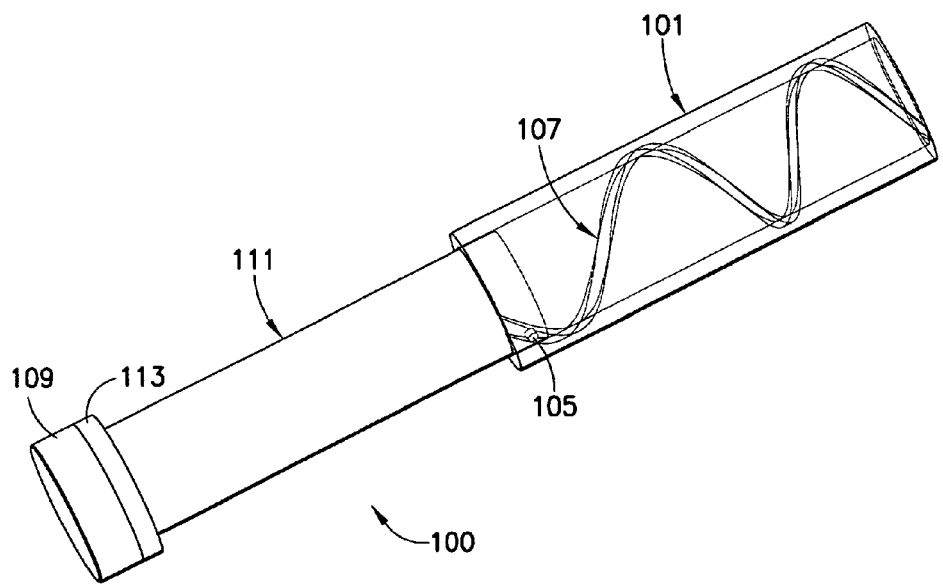
Figure 6:
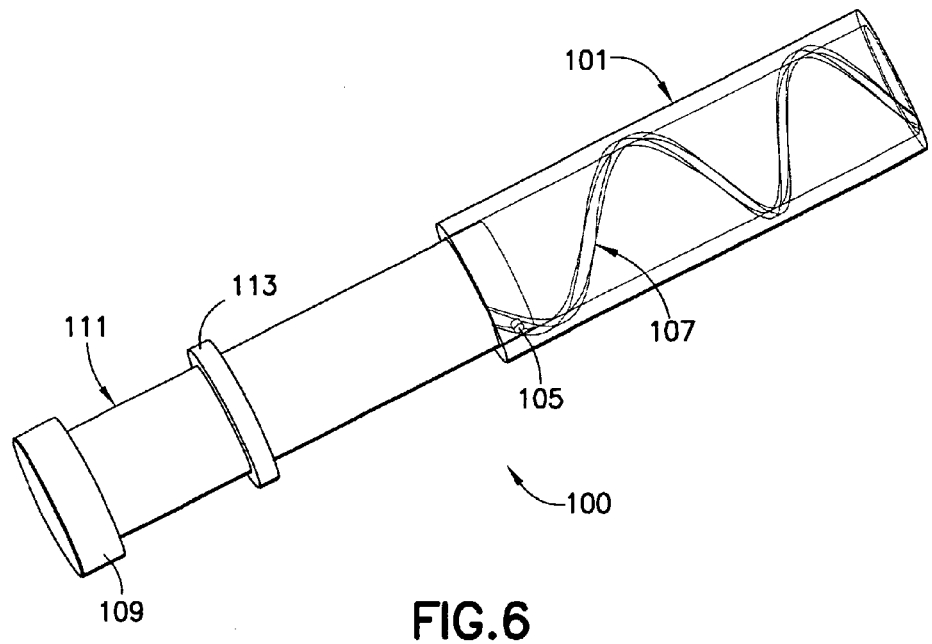
Figure 7:
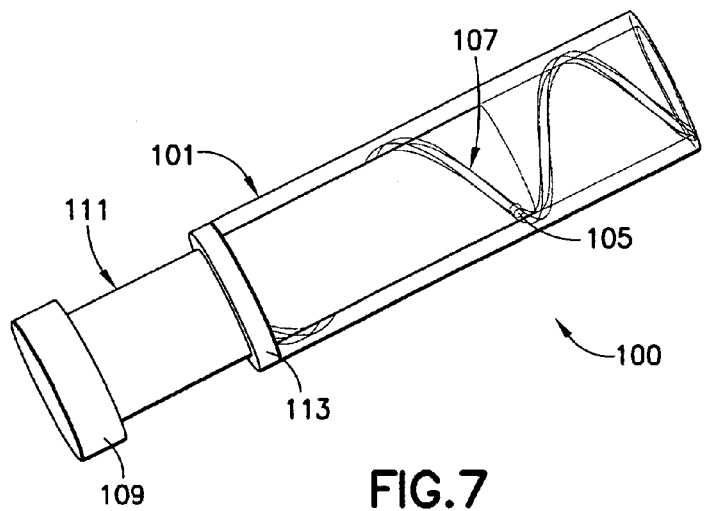

In an exemplary embodiment of a pen body assembly 100 of the present invention, as shown in FIGS. 4-7, the variable pitch thread groove 107 is disposed on the pen body 101. The dose setting knob body 111 and the pen body 101 engage each other through a thread groove 107 and a protrusion 105. As shown in FIG. 5, the dose setting knob 109 and collar 113 are pulled substantially entirely out of the pen body 101. The collar 113 is then moved to a position on the knob body 111 corresponding to the desired dose, as shown in FIG. 6. The dose setting knob 109 is then pushed into the threaded pen body 101 to intradermally inject the medication, as shown in FIG. 7. Pushing the dose setting knob 109 of the dose setting body 111 toward the pen body 111 causes the protrusion 105 to move along the thread groove 107, thereby moving the leadscrew 221 (FIGS. 8-11) outwardly (away from the dose setting knob) through the cartridge 12 disposed in the lower housing 17 (FIG. 2). The collar 113 prevents further inward movement of the knob body 111 into the threaded pen body 101 when the collar 113 abuts the pen body 101. Although not shown in FIGS. 4-7, the pen body assembly 100 includes structure similar to that shown in FIGS. 8-11 downwardly of the pen body, such as the threaded portion for connecting to the lower housing, retraction nut 241 and the leadscrew 221.

Figure 20:
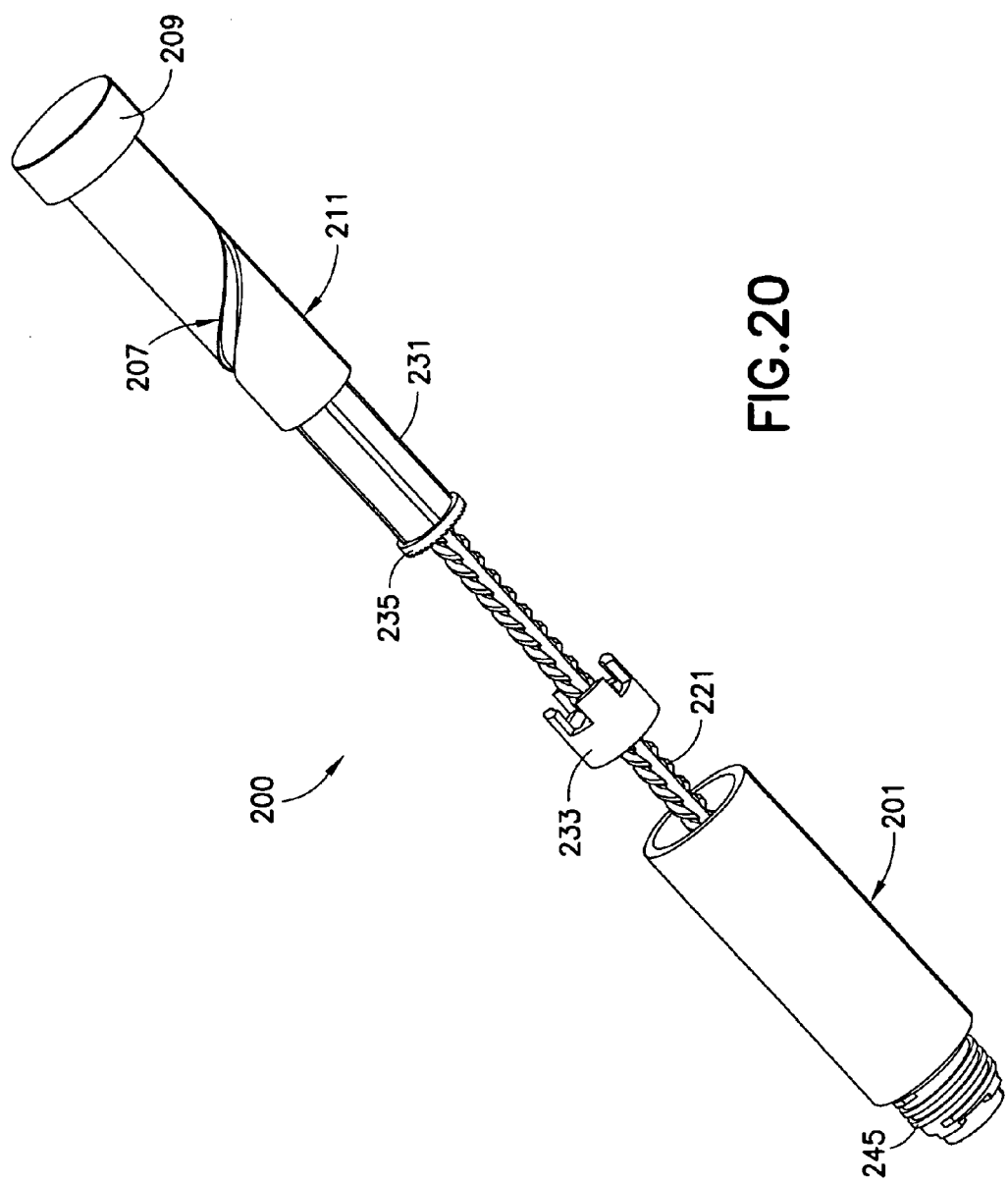
FIG. 20 is an exploded perspective view of a pen body assembly according to the exemplary embodiments of FIGS. 8-11.

As shown in FIG. 20, the variable pitch thread groove 207 of the knob body 211 receives a protrusion 205 (FIG. 8), thereby keying the knob body to the pen body 201. The inner sleeve 231 is keyed to the knob body 211, such that the inner sleeve rotates with the knob body. A nut 233 is keyed to the leadscrew 221.

When the knob body 211 is pushed inwardly toward the pen body 201, the knob body 211 is rotated through the pen body 201 by the variable pitch thread groove 207 traveling over the protrusion 205 (FIG. 8). As the knob body 211 rotates inwardly, the inner sleeve 231 rotates inwardly with the knob body. By disposing the larger pitch portion of the variable pitch thread groove 207 at the beginning of the injection, less force is required by the user to overcome the large backpressure associated with an intradermal injection. The larger pitch results in less axial movement of the leadscrew 221, while increasing the force at the end of the leadscrew. If a larger dose is being made, the protrusion gradually transitions to the smaller pitch portion of the variable pitch thread groove, thereby reducing the force at the end of the leadscrew (because the backpressure has already been overcome) and increasing the axial movement of the leadscrew. The entire length of the variable pitch thread groove (C plus D in FIG. 8) corresponds to a maximum dose. An end 235 of the inner sleeve 231 contacts the nut 233 keyed to the leadscrew 221 and advances the leadscrew axially (without rotation) through the cartridge 12 (FIG. 2). The cartridge 12 is disposed in a lower housing 17, which is threadably engaged with the threaded portion 245 of the pen body 201. When another injection is to be made, the knob body 221 is rotated outwardly without moving the inner sleeve 231.

The thread groove 107 of the pen body has a variable pitch, preferably including a larger pitch portion A that gradually transitions to a smaller pitch portion B, as shown in FIG. 4. The larger pitch portion A is preferably at the beginning of the injection (proximal the dose setting knob 109), such that during the injection the beginning portion of the drug delivery requires relatively lower force because of the higher mechanical advantage.

To amplify the force at the dose setting knob 109 when keeping the leadscrew 121 travel distance constant, the travel distance of the dose setting knob 109 should be increased. When the dose setting knob travel distance is being kept constant, the travel distance of the leadscrew should be decreased.

In another exemplary embodiment of a pen body assembly 200 of the present invention, as shown in FIGS. 8-11, the variable pitch thread groove 207 is disposed on the knob body 211. A protrusion 205 disposed on the pen body 201 engages the thread groove 207. As shown in FIG. 9, the dose setting knob 209 and collar 213 are pulled substantially entirely out of the pen body 201. The collar 213 is then disposed on the threaded knob body 211 to the desired dose, as shown in FIG. 10. The dose setting knob 209 is then pushed inwardly to intradermally inject the medication, as shown in FIG. 11. The collar 213 prevents further inward movement of the threaded knob body 211 into the pen body 201.

The thread groove 207 of the knob body 211 has a variable pitch, preferably including a larger pitch portion C that gradually transitions to a smaller pitch portion D as shown in FIG. 8. The larger pitch portion C is preferably at the beginning of the injection (proximal the pen body 201), such that during the injection the beginning portion of the drug delivery requires relatively lower force because of the higher mechanical advantage. The smaller pitch portion D is preferably at the end of the injection, such that the smaller pitch portion is proximal the dose setting knob 209.

A threaded body portion 245 extends outwardly from an end of the pen body 201, as shown in FIGS. 8-11. The threaded body portion 245 is adapted to engage the lower body housing 17, which receives the cartridge 12 (FIG. 2). A retraction ring 241 allows retraction of the leadscrew 221 into the pen body assembly 200 after a cartridge 12 (FIG. 2) is removed. The leadscrew 221 is retracted into the pen body assembly until an end 223 of the leadscrew contacts an end 243 of the retraction nut 243.

Figure 18:
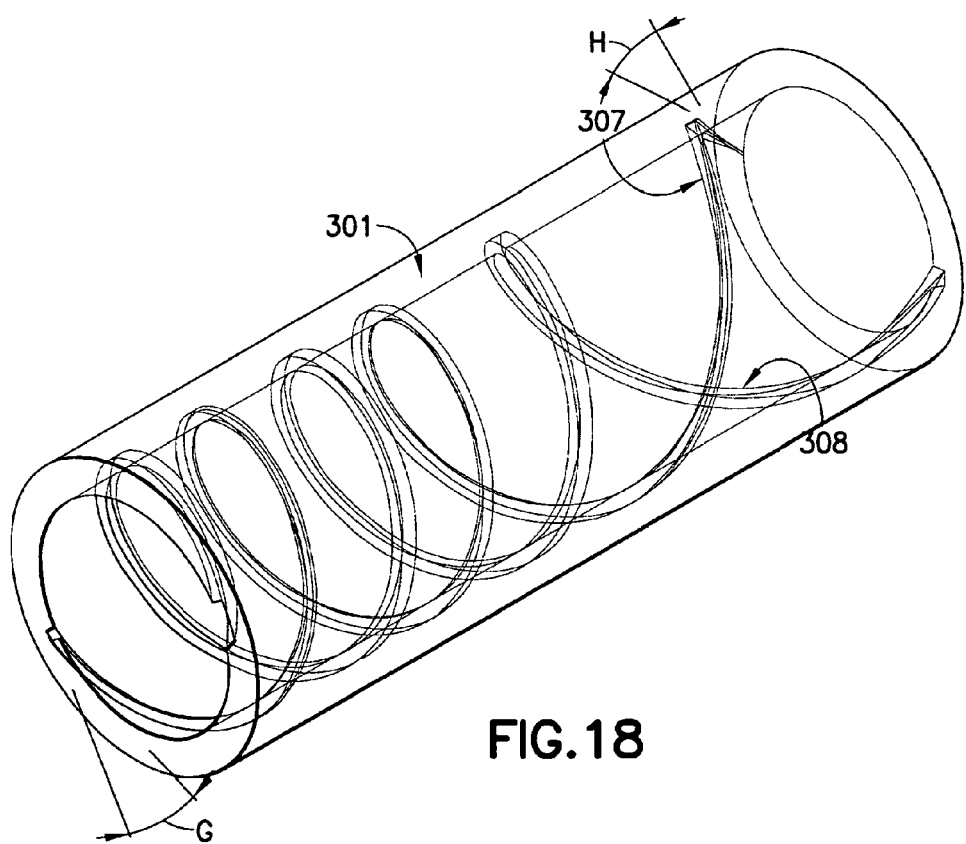
FIG. 18 is a perspective view of a thumb screw having two variable pitch thread grooves.
Figure 19:
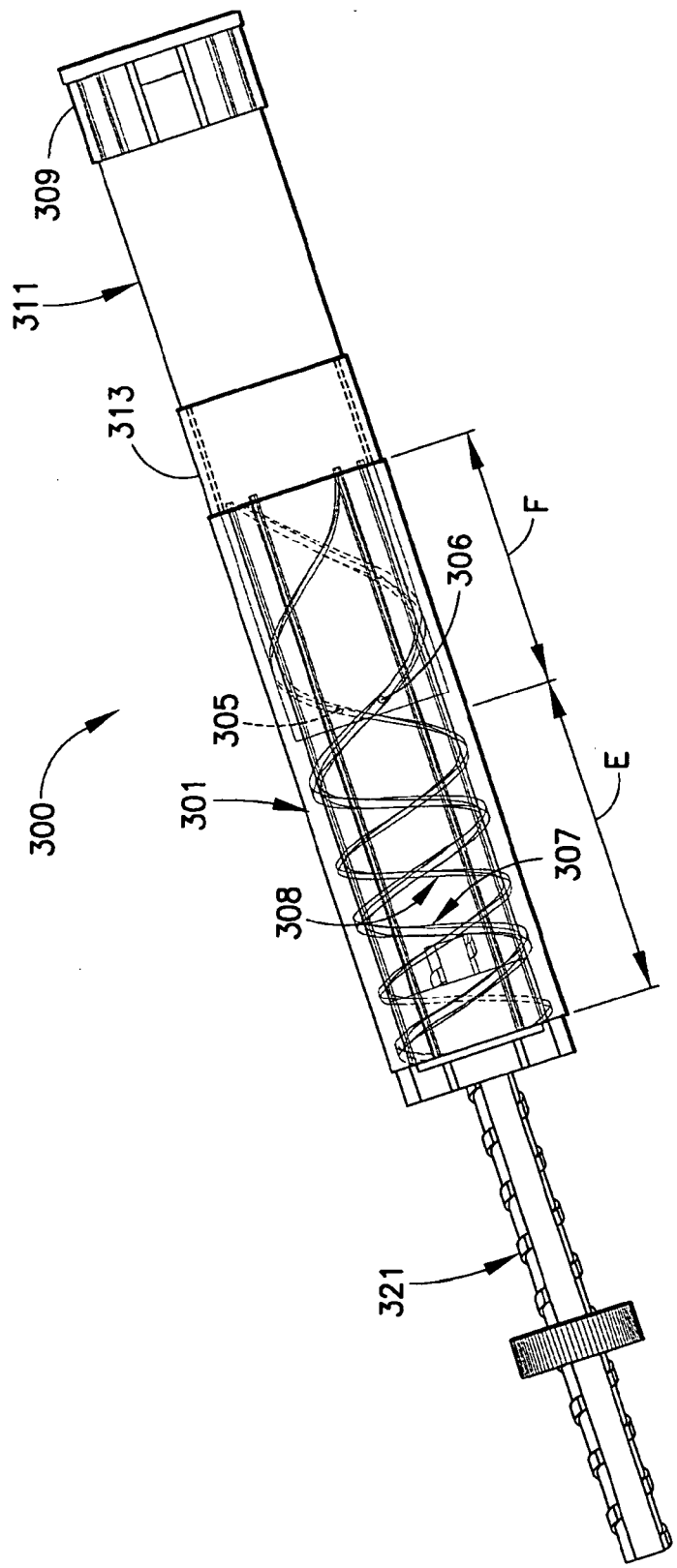
FIG. 19 is a perspective view of a pen body assembly in which the pen body has a pair of variable pitch thread grooves.

In another exemplary embodiment of the present invention, as shown in FIGS. 18 and 19, a pen body assembly 300 has first and second variable pitch thread grooves 307 and 308 disposed approximately 180 degrees apart. First and second grooves 307 and 308 facilitate balancing the force by using two oppositely disposed varied pitch thread grooves. The exemplary embodiment of FIGS. 18 and 19 is substantially similar to the exemplary embodiments of FIGS. 4-11, except for the addition of a second variable pitch thread groove.

The first and second variable pitch thread grooves 307 and 308 are disposed on the pen body 301. Alternatively, the first and second thread grooves 307 and 308 may be disposed on the knob body 311. First and second protrusions 305 and 306 diametrically disposed on the knob body 311 engage the first and second thread grooves 307 and 308, respectively. As shown in FIG. 19, the collar 313 is disposed on the threaded knob body 311 to a position corresponding to the desired dose. The dose setting knob 309 is then pushed inwardly to intradermally inject the medication. The collar 313 prevents further inward movement of the threaded knob body 311 into the pen body 301.

The first and second thread grooves are substantially similar, except for being disposed 180 degrees apart on the pen body 301. The first thread groove 307 of the knob body 311 has a varied pitch, preferably including a larger pitch portion F and a smaller pitch portion E as shown in FIG. 19. The larger pitch portion F is preferably at the beginning of the injection (proximal the dose setting knob 309), such that during the injection the beginning portion of the drug delivery requires relatively lower force because of the higher mechanical advantage. The smaller pitch portion E is preferably at the end of the injection, such that the smaller pitch portion is proximal the leadscrew 321.

Various modifications to increase the force at the leadscrew are shown in Table I, including possible trade-offs for such modifications.

TABLE I

| Component | Possible Modification to Increase Force | Possible Trade-Off |
|---|---|---|
| Dose Set Knob | Increase Pitch | Reduced max dose |
|  | Increase Outer Diameter | Increase device size |
| Driver | Increase Outer Diameter | Increase device size |
| Leadscrew | Reduce Pitch | Increase friction |
|  | Reduce Diameter | Reduce mechanical strength |
| Reset Ring | Increase Diameter | Increase device size |
|  | Increase Engage Interface of Teeth | Increase friction |
| Retraction Nut | Reduce Lock Interface Area | Reduce mechanical strength |

Figure 12:
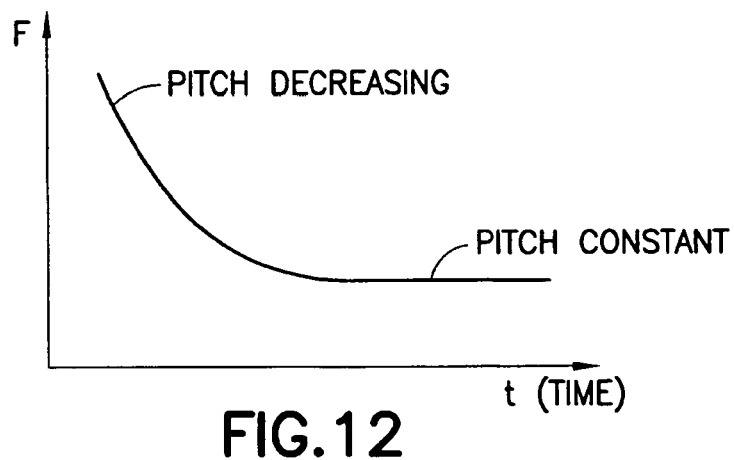
FIGS. 12-14 are graphs of the force profile for intradermal medication deliveries with different pitch designs.
Figure 13:
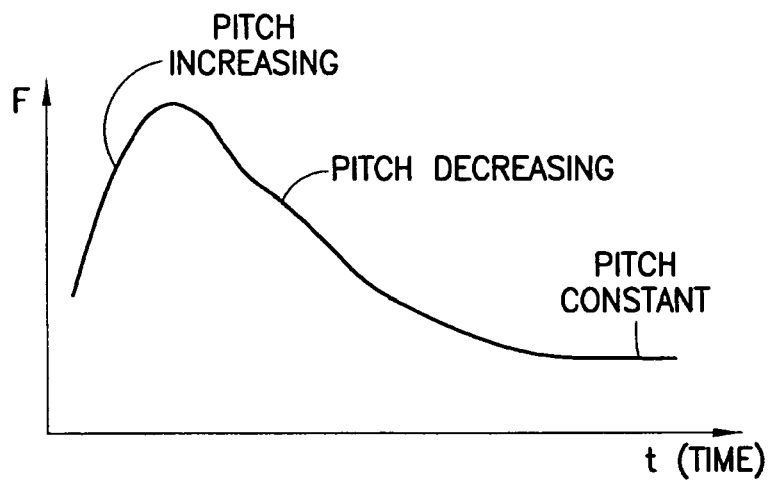
Figure 14:
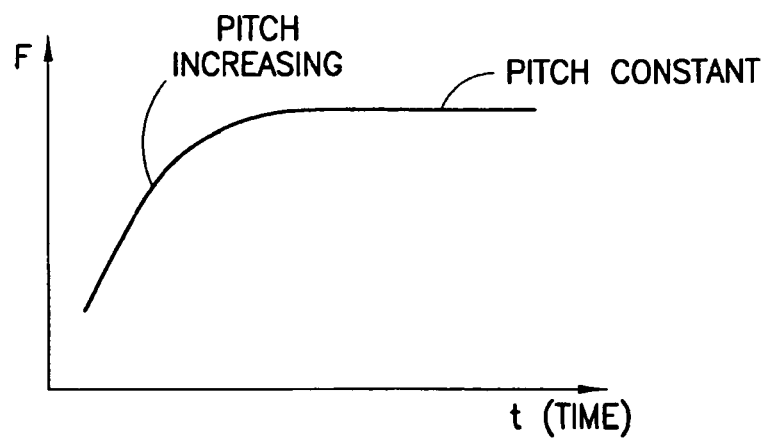

FIGS. 12-14 are graphs of the force profile for various variable pitch thread designs with constant input force from the user. As shown in FIG. 12, decreasing the pitch over time decreases the resulting force. As shown in FIG. 13, the force increases with increasing pitch and then the force decreases with decreasing pitch. As shown in FIG. 14, the force increases with increasing pitch. By having a varied pitch thread design, when the dose setting knob is moving at a constant speed, the leadscrew moving speed is not constant.

Fundamentally, the mechanical advantage is defined as the ratio of output force over input force. Furthermore, from "work-in"=$\eta \times$"work-out", where $\eta$ is the system efficiency. Thus, work-in=force-in×(displacement at input).

Work-out=(force-out at plunger end on cartridge stopper)×(displacement of cartridge stopper during injection).

User input force is denoted Ft pushing down on a button 209 that has displacement St, at the output. The plunger 221 (drive screw in the drug delivery pen) force Fp is applied on the cartridge stopper 15 (FIG. 2) and moves the stopper a distance (displacement St).

Assuming an ideal system, that is, 100% efficiency, the work-in equals the work-out. Thus, Ft×St=Fp×Sp. Or, Fp/Ft=St/Sp.

The mechanical gain A is defined as A=Fp/Ft. This indicates that a displacement ratio of St/Sp=A, which means the thumb screw displacement is large while the plunger displacement is small.

Assuming the system has an efficiency of $\eta$ due to friction, then Ft×St=$\eta$×Fp×Sp. Thus, St/Sp=A/$\eta$.

Figure 15:
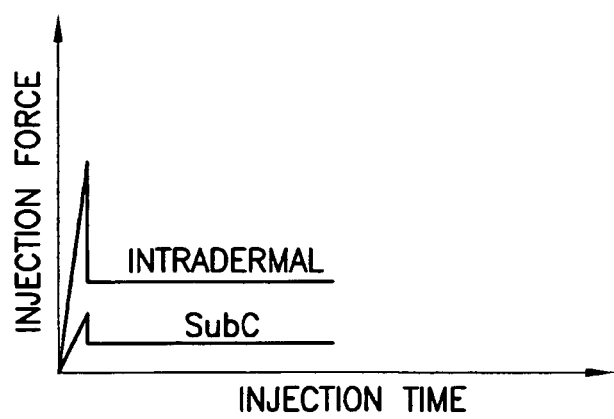
FIG. 15 is a graph of the required injection force for intradermal and subcutaneous injections.

The drug delivery pen accordingly to an exemplary embodiment of the present invention can have a much larger mechanical gain to allow a user to apply a comfortable thumb force, for example, 2.5 lbf, and to amplify the applied force up to a higher force, for example, 20 lbf, on the cartridge stopper. However, the higher force is preferably only needed during the first stage of the injection, i.e., the breakout force. After the initial breakout, the injection force is reduced to a significantly lower level and is substantially constant through the end of the injection, as shown in FIG. 15, which compares the injection force profiles for intradermal and subcutaneous injections. As shown in FIG. 15, the subcutaneous profile is relatively constant, but the intradermal injection has distinguished two stages. An exemplary embodiment of the present invention matches the mechanical gain to the profile so that the required mechanical gain is delivered in accordance with the injection stage.

The thumb screw has two pitch settings, a coarse (or larger) pitch for the first stage driving and a finer (or smaller) pitch for the second stage driving. The screw diameter remains the same. Preferably, the screw diameter is approximately 6 mm, the coarse pitch angle has a lead angle H (FIG. 18) of approximately 39 degrees such that one revolution provides a 15 mm lead, and the finer pitch angle has a lead angle G (FIG. 18) of approximately 15 degrees over 7 revolution turns. The total dose range provided is approximately 50 U. The total thumb screw length is approximately 50 mm.

Figure 16:
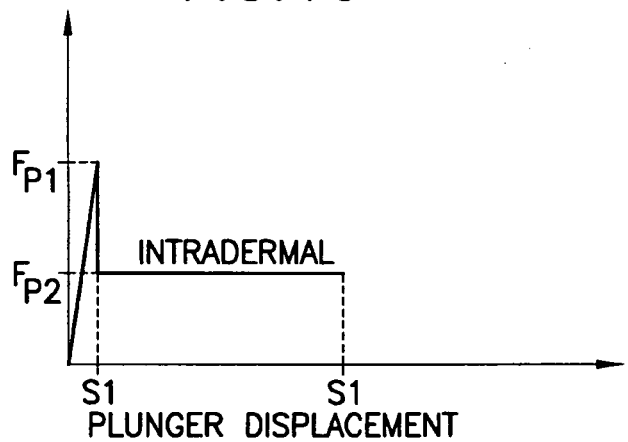
FIG. 16 is a graph of the required injection force for an intradermal injection showing the first and second stages.

As shown in FIG. 16, an intradermal injection profile force has two stages. The travel of the thumb screw matches the work needed to move the cartridge stopper. Thus, Ft1×St1=Fp1×S1. Similarly, Ft2×St2=Pp1×(S2−S1). Ft1 and Ft2 are the thumb button forces in stage 1 and stage 2, respectively, of the intradermal injection. The thumb screw travel displacement is St=n×Lt, where n is the number of turns the screw turns during the injection stage and Lt is the lead of the screw. When it is a single thread, the lead equals the pitch of the lead screw.

The lead screw has a lead angle $\theta$, thread angle $\beta$ and diameter D. The relationship between the lead L and the lead angle $\theta$ is L=$\pi$×D tan $\theta$.

The drive screw is used to raise a load so for best efficiency the lead angle is small, but large enough to prevent self-locking. Also, the small lead angle is needed for small displacement at the plunger output.

The thumb screw, however, has a variable pitch or variable diameter design, or a combination thereof. This provides the mechanical advantage based on the demand profile.

A 3 mL cartridge has an inner diameter Dc=9 mm. The breakout peak force typically occurs at delivering 50 μL volume. Thus, S1=breakout volume/($\pi Dc^2/4$)=0.786 mm. Therefore, when the mechanical gain in the first stage is 20, St1=20×0.786=15.72 mm. The thumb screw is used to lower the load. The coefficient of efficiency $\eta t1$ is related to the lead angle, thread angle and diameter of the screw as follows: $\eta t1$=tan $\theta t1$(cos $\beta$−μ tan $\theta t1$)/(cos $\beta$ tan $\theta t1$+μ), where μ is the coefficient of friction.

Figure 17:
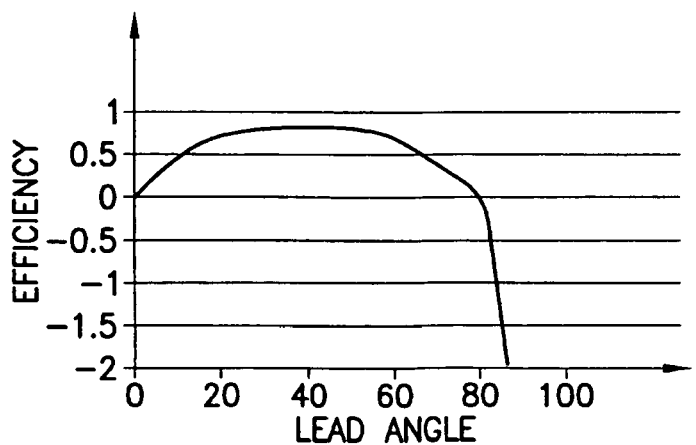
FIG. 17 is a graph of efficiency vs. lead angle.

To increase efficiency, $\beta$ should be small, such as, for example, approximately 5 degrees, such that cos $\beta$ is approximately 1. A typical plastic material has μ=0.2. Thus, the relationship of efficiency vs. the lead angle is as shown in FIG. 17. The maximum efficiency is about 0.67, when $\theta$=39 degrees. Thus, when tan $\theta t1$=0.81, St1=nt1 tan $\theta t1$×$\pi$Dt1, where nt1 is the number of turns. When nt1=1, Dt1=6 mm.

When the required dose range is 500 μL and the lead angle is not changed, the number of turns should be approximately 10. This results in a total length of 150 mm, which is not practical. Preferably, the length limitation is approximately 50 mm. After the first stage delivery using a coarse pitch angle of 15 mm, 35 mm of travel distance is left. The newly required mechanical gain is 5, such that St2=5×(7.86-0.786)=35.37 mm. If the same diameter of 6 mm is used, 0=15 degrees, and efficiency is 0.54, then nt2=7 turns.

An additional advantage of this exemplary embodiment is to more finely titrate a dose. As the mechanical advantage increases, the stroke required to deliver some fixed dose also increases. Thus, smaller injections may be controlled for a given stroke length. This is of particular interest with insulin delivery where a patient finely tunes their dose size to the narrow therapeutic window of the drug.

In another exemplary embodiment, the thumb screw has two sections. The first section has a larger diameter and coarser pitch for the first driving stage. The second section has a smaller diameter and finer pitch for the second driving stage, which requires a smaller force. Alternatively, the thumb screw has two telescoping sections. One section has a coarser pitch and the other section has a finer pitch.

In another exemplary embodiment of the present invention, a drug delivery pen has a variable lead angle and diameter on a thumb screw to generate mechanical advantage based on demand. The pen injector system has two lead screws. The thumb screw translates thumb button input force to torque. The drive screw translates the torque applied to the thumb screw via the thumb button to the plunger output force, which is applied to the cartridge stopper, thereby delivering the medication.

The foregoing embodiments and advantages are merely exemplary and are not to be construed as limiting the scope of the present invention. The description of exemplary embodiments of the present invention is intended to be illustrative, and not to limit the scope of the present invention. Various modifications, alternatives and variations will be apparent to those of ordinary skill in the art, and are intended to fall within the scope of the invention as defined in the appended claims and their equivalents.

The invention claimed is:

1. A pen body assembly for a drug delivery pen, comprising:
    a pen body including a first thread groove with a variable pitch having a larger pitch portion and a smaller pitch portion;
    a dose setting body movably connected to said pen body including a protrusion engaging said first thread groove;
    a knob connected to said dose setting body for moving said dose setting body relative to said pen body; and
    a collar movably connected to said dose setting body and limiting movement of said dose setting body through said pen body; wherein
    said larger pitch portion is proximal to said knob relative to said smaller pitch portion; and
    said collar is disposed between said knob and said pen body.

2. A pen body assembly for a drug delivery pen according to claim 1, wherein
    a lead angle of said larger pitch portion is approximately 39 degrees.

3. A pen body assembly for a drug delivery pen according to claim 1, wherein
    a lead angle of said smaller pitch portion is approximately 15 degrees.

4. A pen body assembly for a drug delivery pen according to claim 1, wherein
    a second variable pitch thread groove is substantially identical to said first variable pitch thread groove and is disposed 180 degrees offset therefrom.

5. A pen body assembly for a drug delivery pen according to claim 4, wherein
    a second protrusion is disposed diametrically opposite to said first protrusion and engages said second variable pitch thread groove.

6. A drug delivery pen, comprising:
    a pen body having a protrusion;
    a dose setting body movably connected to said pen body including a first thread groove with a variable pitch having a larger pitch portion and a smaller pitch portion engaging said protrusion;
    a cartridge connected to said pen body;
    a lead screw movably disposed within said cartridge and movably connected to said dose setting body;
    a knob connected to said dose setting body for moving said dose setting body relative to said pen body; and
    a collar movably connected to said dose setting body and limiting movement of said dose setting body through said pen body; wherein
    said larger pitch portion is proximal to said pen body relative to said smaller pitch portion; and
    said collar is disposed between said knob said pen body.

7. A pen body assembly for a drug delivery pen according to claim 6, wherein
    a lead angle of said larger pitch portion is approximately 39 degrees.

8. A pen body assembly for a drug delivery pen according to claim 6, wherein
    a lead angle of said smaller pitch portion is approximately 15 degrees.

9. A pen body assembly for a drug delivery pen according to claim 6, wherein
    a second variable pitch thread groove is substantially identical to said first variable pitch thread groove and is disposed 180 degrees offset therefrom.

10. A pen body assembly for a drug delivery pen according to claim 9, wherein
    a second protrusion is disposed diametrically opposite to said first protrusion and engages said second variable pitch thread groove.

* * * * *